US00PP21293P2

(12) United States Plant Patent
Smith

(10) Patent No.: US PP21,293 P2
(45) Date of Patent: Sep. 14, 2010

(54) ***CHRYSANTHEMUM* PLANT NAMED 'CRAZY YOVICTORIA'**

(50) Latin Name: *Chrysanthemum×morifolium*
Varietal Denomination: Crazy Yovictoria

(75) Inventor: Mark A. Smith, Fort Myers, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/459,538

(22) Filed: Jul. 2, 2009

(51) Int. Cl.
*A01H 5/00* (2006.01)

(52) U.S. Cl. ..... Plt./287

(58) Field of Classification Search ..... Plt./287, Plt./290

See application file for complete search history.

*Primary Examiner*—June Hwu
(74) *Attorney, Agent, or Firm*—S. Matthew Edwards

(57) ABSTRACT

A new *Chrysanthemum* plant named 'Crazy Yovictoria,' particularly distinguished by the small, decorative-type, bi-colored orange and yellow flowers; medium green foliage; freely branching, with a compact and mounded plant habit.

1 Drawing Sheet

Latin name of the genus and species of the plant claimed: *Chrysanthemum×morifolium.*

Varietal denomination: 'Crazy Yovictoria'.

BACKGROUND OF THE NEW PLANT

The present invention comprises a new *Chrysanthemum*, botanically known as *Chrysanthemum×morifolium*, and hereinafter referred to by the variety name 'Crazy Yovictoria'.

The new cultivar 'Crazy Yovictoria' has small, decorative-type, bi-colored orange and yellow flowers; medium green foliage; freely branching, with a compact and mounded plant habit.

'Crazy Yovictoria' originated as a natural whole plant mutation of 'Delightful Yovictoria,' U.S. Patent Pat. No. 17,450. 'Crazy Yovictoria' was discovered and selected by the inventor as a single flowering plant within a population of the parent cultivar in a field trial in Alva, Fla. in December 2005. The parent cultivar 'Delightful Yovictoria' has darker orange flowers; natural season response and greenhouse black cloth flowering response is about 2 days faster.

The first act of asexual reproduction of 'Crazy Yovictoria' was accomplished when vegetative cuttings were propagated from the initial selection in January 2006 in a controlled environment in Alva, Fla.

BRIEF SUMMARY OF INVENTION

Horticultural examination of plants grown from cuttings of the plant initiated in January 2006 and continuing thereafter, has demonstrated that the combination of characteristics as herein disclosed for 'Crazy Yovictoria' are firmly fixed and are retained through successive generations of asexual reproduction.

'Crazy Yovictoria' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Chrysanthemum* as a new and distinct variety.

Plant Breeder's Rights for this cultivar have not been applied for. 'Crazy Yovictoria' has not been made publicly available more than one year prior to the filing of this application.

BRIEF DESCRIPTION OF THE PHOTOGRAPHS

Figure 1:
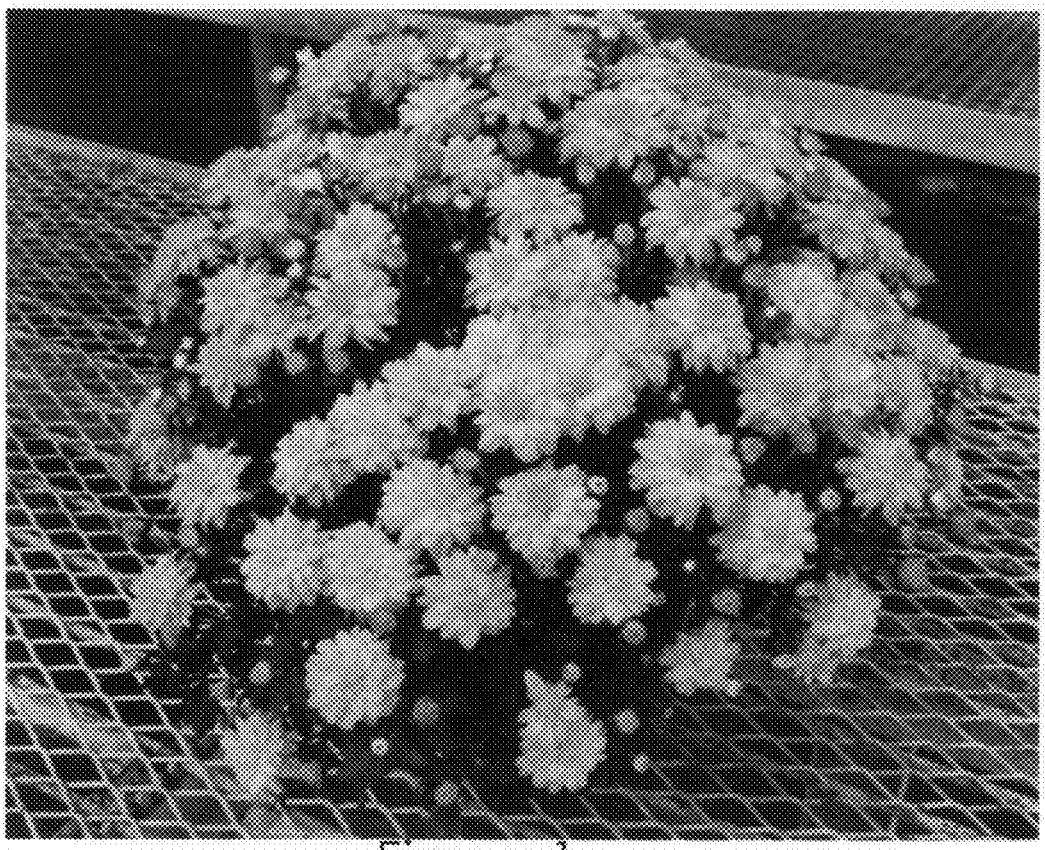
Figure 2:
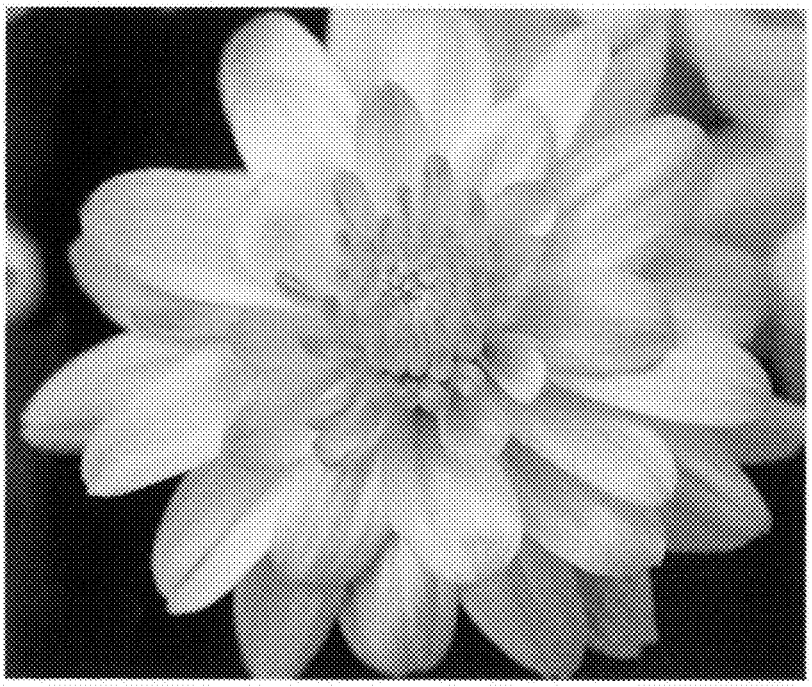

The accompanying photographic drawing shows typical flower and foliage characteristics of 'Crazy Yovictoria' with colors being as true as possible with an illustration of this type. The photographic drawing shows in FIG. 1 a flowering potted plant of the new variety, and in FIG. 2 a close-up of the flowers.

DETAILED BOTANICAL DESCRIPTION

The plant descriptions and measurements were taken in Salinas, Calif. in early June, 2009 under natural light. The aforementioned photographs were taken in Gilroy, Calif. in early June, 2009 in a greenhouse. These plants were started and grown in six inch pots in Alva, Fla. and were shipped to California in late May, 2009.

Plants were grown under conditions which approximate those generally used in commercial potted *Chrysanthemum* production. These plants used in the photograph and descriptions were about 10 weeks old.

Color references are made to The Royal Horticultural Society Colour Chart (R.H.S.) 2001.

TABLE 1

DIFFERENCES BETWEEN THE NEW VARIETY 'CRAZY YOVICTORIA' AND A SIMILAR VARIETY

| | 'Crazy Yovictoria' | 'Yogigi Gold' (U.S. Plant Pat. No. 19,631) |
|---|---|---|
| Flower color: | More orange and yellow | Mostly golden yellow |
| Flower size: | Little larger flower | Little smaller flower |
| Quantity of disc florets: | Fewer | More |
| Flowering habit: | Fuller and more uniform | Less full and uniform |
| Plant size: | Larger | Smaller |

Plant:

*Form, growth and habit.*—Herbaceous decorative garden-type; stems upright and outwardly spreading, freely branching, strong and moderately vigorous growth habit.

*Plant height.*—25-27 cm.

*Plant height (inflorescence included).*—28-29 cm.

*Plant width.*—35-45 cm.

*Garden performance and tolerance to weather.*—Good.

*Crop time to flowering.*—About 43-45 days.

Roots:

*Number of days to initiate roots.*—4 days at about 21 degrees C.

*Number of days to produce a rooted cutting.*—10-12 days at 21 degrees C.

*Type.*—Fine, fibrous, free branching.

*Color.*—RHS N155B but whiter.

Foliage:

*Arrangement.*—Alternate, simple.

*Immature, leaf color, upper surface.*—Closest to RHS 137A but lighter.

*Lower surface.*—Closest to RHS 146A.

*Mature, leaf color, upper surface.*—Closest to RHS 137A but lighter.

*Lower surface.*—Closest to RHS 146A.

*Length.*—4.5-5.5 cm.

*Width.*—3.8-4.2 cm.

*Shape.*—Ovate.

*Base shape.*—Attenuate.

*Apex shape.*—Mucronulate.

*Margin.*—Palmately lobed; slightly incised and serrate.

*Texture, upper surface.*—Bifid T-shaped hairs.

*Lower surface.*—Bifid T-shaped hairs.

*Color of veins, upper surface.*—RHS 146D.

*Color of veins, lower surface.*—RHS 146D.

*Petiole color.*—RHS 146D.

*Length.*—1.2-1.4 cm.

*Diameter.*—0.25 cm.

*Texture.*—Bifid T-shaped hairs.

Stem:

*Quantity of main branches per plant.*—8-9.

*Quantity of leaves per branch.*—10-12.

*Color of stem.*—RHS 146B.

*Length of stem.*—17-18 cm.

*Diameter.*—0.4 cm.

*Length of internodes.*—0.5 cm.

*Texture.*—Bifid T-shaped hairs.

*Color of peduncle.*—RHS 146B but appears lighter with the heavy amount of hairs.

*Length of peduncle.*—5.5-6.5 cm.

*Peduncle diameter*—0.15-0.2 cm.

*Texture.*—Bifid T-shaped hairs.

Inflorescence:

*Type.*—Compositate type, solitary inflorescences (decorative-type) borne terminally above foliage, ray florets arranged acropetally on a capitulum.

*Blooming habit.*—Natural season flowering around mid-September.

*Quantity of inflorescences per plant.*—About 250.

*Quantity of inflorescences per lateral stem.*—About 50.

*Lastingness of individual blooms on the plant.*—4 weeks.

*Fragrance.*—Slightly spicy.

Bud (just before opening/showing color):

*Color.*—RHS 175B with RHS 175A at the apex.

*Length.*—0.6-0.8 cm.

*Width.*—0.7-0.8 cm.

*Shape.*—Oblate.

Immature inflorescence:

*Diameter.*—2.5 cm.

*Color of ray florets, upper surface.*—RHS 7A basally, with between RHS 175B and RHS 175C margins and apex.

*Lower surface.*—RHS 3A basally, with between RHS 175C and RHS 175D margins and apex.

Mature inflorescence:

*Diameter.*—3.6-3.8 cm.

*Depth.*—2.2-2.5 cm

*Total diameter of 'disc'.*—No 'disc' showing.

*Receptacle height.*—0.3-0.4 cm.

*Receptacle diameter.*—0.2-0.25 cm.

Ray florets:

*Average quantity of florets.*—About 100 in numerous whorls.

*Color of florets, upper surface.*—RHS 7B basally; varying hues of RHS 175C towards the apex that fades with maturity to about RHS 173B.

*Lower surface.*—RHS 4A with between RHS 172C to RHS 172D at the apex and margins.

*Length.*—1.0-1.2 cm.

*Width.*—0.5-0.6 cm.

*Shape.*—Oblong.

*Apex shape.*—Emarginate to slightly praemorse.

*Margin.*—Entire.

*Texture, upper surface.*—Papillose.

*Lower surface.*—Papillose.

Disc florets:

*Average quantity of florets.*—About 2.

*Color of florets.*—RHS 1C with RHS 2B at the apex.

*Length.*—0.2 cm.

*Width.*—0.1 cm.

*Shape.*—Tubular.

*Apex shape.*—Acute, 5 pointed.

Phyllaries:

*Quantity.*—10-12.

*Color, upper surface.*—Closest to RHS 147B.

*Lower surface.*—Closest to RHS 147B.

*Length.*—0.4-0.65 cm.

*Width.*—0.15-0.2 cm.

*Shape.*—Lanceolate.

*Apex shape.*—Acute.

*Based.*—Fused.

*Margins.*—Entire; papery and translucent.

*Texture, upper surface.*—Bifid T-shaped hairs.

*Lower surface.*—Bifid T-shaped hairs.

Reproductive organs:

*Gynoecium.*—Found on both floret types.

*Pistil quantity.*—1.

*Length.*—0.5 cm.

*Style color.*—RHS 1C.

*Style length.*—0.4 cm.

*Stigma color.*—RHS 1A.

*Stigma shape.*—Bi-parted.

*Ovary color.*—RHS 155C.

*Androecium.*—Found on only disc florets.

*Stamen quantity.*—4-5.

*Color of filaments.*—RHS 1C.

*Length filaments.*—0.1 cm.

*Anther color.*—RHS 1A.

*Anther length.*—0.1 cm.

*Anther shape.*—Ligulate.

*Color of pollen.*—Not observed (too immature).

*Pollen amount.*—Not observed (too immature).

*Fertility/seed set.*—Has not been observed on this hybrid

Disease/pest resistance: Disease resistance or susceptibility has not been observed on this hybrid.

What is claimed is:

1. A new and distinct variety of *Chrysanthemum* plant named 'Crazy Yovictoria,' substantially as illustrated and described herein.

* * * * *